United States Patent
Osterdahl et al.

(10) Patent No.: US 7,353,949 B2
(45) Date of Patent: Apr. 8, 2008

(54) PACKAGING UNIT

(75) Inventors: Eje Osterdahl, Vastra Frolunda (SE);
Pontus Winqvist, Stora Hoga (SE);
Roy Hansson, Molndal (SE)

(73) Assignee: SCA Hygiene Products AB, Gothenburg (SE)

( * ) Notice: Subject to any disclaimer, the term of this patent is extended or adjusted under 35 U.S.C. 154(b) by 497 days.

(21) Appl. No.: 10/905,328

(22) Filed: Dec. 28, 2004

(65) Prior Publication Data
US 2006/0138010 A1 Jun. 29, 2006

Related U.S. Application Data

(60) Provisional application No. 60/532,952, filed on Dec. 30, 2003.

(51) Int. Cl.
*B65D 73/00* (2006.01)
(52) U.S. Cl. .................. 206/494; 206/440; 53/429; 53/447; 53/475
(58) Field of Classification Search ........... 206/440, 206/494, 497, 499, 812; 604/385.201; 53/429, 53/434, 447, 475, 438
See application file for complete search history.

(56) References Cited

U.S. PATENT DOCUMENTS

| 4,934,535 | A | | 6/1990 | Muckenfuhs et al. | |
|---|---|---|---|---|---|
| 4,966,286 | A | * | 10/1990 | Muckenfuhs | 206/494 |
| 5,036,978 | A | * | 8/1991 | Frank et al. | 206/494 |
| 5,163,558 | A | * | 11/1992 | Palumbo et al. | 206/494 |
| 5,413,568 | A | * | 5/1995 | Roach et al. | 604/358 |
| 6,079,562 | A | * | 6/2000 | Bauer et al. | 206/494 |
| 6,926,149 | B2 | * | 8/2005 | Tippey | 206/494 |
| 2004/0134822 | A1 | * | 7/2004 | Otsubo | 206/440 |
| 2004/0173490 | A1 | * | 9/2004 | Otsubo | 206/440 |
| 2004/0195137 | A1 | * | 10/2004 | Otsubo | 206/494 |
| 2005/0077200 | A1 | * | 4/2005 | Tippey | 206/440 |

FOREIGN PATENT DOCUMENTS

| EP | 0 122 042 A2 | 10/1984 |
|---|---|---|
| EP | 0 391 460 A1 | 10/1990 |
| EP | 0 406 928 A1 | 1/1991 |
| EP | 0 77 015 A1 | 6/1997 |
| EP | 0 780 325 A1 | 6/1997 |
| EP | 0 947 446 A1 | 10/1999 |
| EP | 1 205 171 A2 | 5/2002 |
| GB | 2 264 278 A | 8/1993 |
| WO | WO 93/16925 A1 | 9/1993 |
| WO | WO 97/33815 A1 | 9/1997 |

OTHER PUBLICATIONS

PCT International-Type Search Report.

* cited by examiner

*Primary Examiner*—David T. Fidei
(74) *Attorney, Agent, or Firm*—Buchanan Ingersoll & Rooney PC (57) ABSTRACT

Packaging unit (17) for absorbent articles (1) including a number of folded articles (1), the folded parts (11) of the articles being arranged towards one of the sides (18) of the packaging unit, but at different distances from the side (18).

52 Claims, 4 Drawing Sheets

PACKAGING UNIT

CROSS-REFERENCE TO RELATED APPLICATIONS

The present application claims the benefit of U.S. Provisional Application No. 60/532,952, filed in the United States on Dec. 30, 2003.

TECHNICAL FIELD

The invention relates to a packaging unit comprising at least one side. The packaging unit comprises a number of absorbent articles, each absorbent article being folded at least once along a substantially transverse fold line, each article having at least one fold area. The fold lines are arranged parallel to the side of the packaging unit, and the fold areas are oriented towards the side of the packaging unit.

BACKGROUND

In the technical field of absorbent articles, considerable efforts have been made over many years to increase the number of manufactured articles, for example babies' diapers or incontinence diapers, per unit of volume for storage and transportation. Nowadays, for example, twice as many babies' diapers are transported by truck as were transported in a similarly sized truck a number of years ago.

Thinner articles, still with a high absorption capacity, represent one of the areas that have been improved. Enhanced thinness has been achieved principally by introduction of gel-forming superabsorbents in increasing concentrations in the absorption cores of the absorbent articles. The articles have thus been improved in terms of their handling both during storage and transportation. Thinner absorbent articles have also been preferred by users, and this fact has of course also prompted various manufacturers to steer developments in this direction.

Thinness has also been achieved by the fact that the articles are nowadays compressed much more than in the past. EP 0,122,042 is one example of a patent which describes how absorbent articles are compressed efficiently so as to achieve increased thinness while at the same time maintaining or even improving the absorption capacity. The patent proposes compressing absorption bodies at a low moisture content in order to maintain softness and pliability despite compression to high density levels (low bulk levels).

More effective ways of packaging absorbent articles have also been developed. The absorbent articles have been packaged with ever greater compression.

Patent application GB 2,264,278 A describes a method for effective compression of a stack, that is to say an individual packaging unit, of absorbent articles in connection with the articles being enclosed in a wrapper. The volume of the packaging is minimized by means of a stack of folded absorbent articles being compressed together with a two-part packaging envelope of the wrapper type. Finally, the absorbent articles are locked in the compressed state by the two parts of the packaging envelope being connected to one another when the absorbent articles are still under external compression.

U.S. Pat. No. 4,934,535 describes an easy-to-open packaging for compressed absorbent articles. The patent also describes how a bag is filled with absorbent articles at the same time as the stack of articles is compressed. When a bag is to be filled with folded absorbent articles, according to the patent, the stack of articles is first compressed by two pressing devices. The pressing devices are then introduced into the bag together with the compressed articles, the articles remaining pressed together throughout the stage of introduction. The surfaces of the pressing devices which are in contact with the stack of articles comprise members which are movable in the depth direction of the bag, and the pressing devices can be removed from the bag without any frictional forces arising between the stack of absorbent articles and the pressing devices. Since no frictional forces arise between the stack of articles and the pressing devices when these are drawn out of the bag, the pressing devices can be removed without any risk of the stack collapsing. When the pressing devices have been removed, the stack of articles is kept under pressure by the sides of the bag. The filling method permits high density of packaging while maintaining a high finish of the packaging.

A problem which is not solved in the patent U.S. Pat. No. 4,934,535 is that of protecting the folded areas of the articles when these are pressed together and stored under high pressure in the packaging.

When a packaging unit comprising absorbent articles folded about one or more substantially transverse fold lines is compressed at right angles to the material layers, the fold areas are the most sensitive areas of the articles. High compression often means that permanent fold notches are formed, and the absorbent article will then have one or more hard and uncomfortable creases when it is being worn by a user. Fold notches also function as channels in which liquid can run, a fact which is particularly unfortunate when the channels extend in the transverse direction of the absorbent article and are located in the area where various body fluids such as urine are collected in the absorbent article.

Compression of other parts of the absorbent articles in the packaging unit, that is to say compression at right angles to the material layers, is not as problematic because no creases or the like are created. In addition, the material layers normally included in absorbent articles have a considerable capacity for recovering their original configuration when the compression ceases, as long as the compression has taken place at right angles to the material layers.

OBJECTS AND SUMMARY

There is therefore still a need for a packaging unit in which the fold areas of the absorbent articles are better protected when the packaging unit is compressed in connection with introduction of the articles into a bag, for example, or upon compression in connection with enclosure in a wrapper.

A packaging unit of the type mentioned in the introduction has been obtained, which packaging unit to a large extent avoids the problems which were associated with previously known packaging units.

A packaging unit designed according to an embodiment of the invention is distinguished principally by the fact that the fold areas of some of the absorbent articles are arranged at a distance from the side of the packaging unit, and the fold areas of others of the absorbent articles are arranged in direct contact with the side of the packaging unit.

By configuring the fold areas of the articles at different levels in the packaging unit, it is possible to avoid a situation where permanent fold notches are created when the articles are pressed together hard during packaging in a bag, for example. Greater packaging density with improved utilization of volume during storage and transportation without the aforementioned disadvantages results.

In one embodiment of the invention, the packaging unit comprises absorbent articles whose substantially transverse fold lines are arranged substantially at the center of the articles in the longitudinal direction of the articles.

In an alternative embodiment of the invention, the packaging unit comprises absorbent articles whose substantially transverse fold lines are arranged at a distance from the center of the articles in the longitudinal direction of the articles.

According to a preferred embodiment, the absorbent articles are also folded about a second substantially transverse fold line, the absorbent articles comprising a second fold area. Articles folded twice are especially advantageous for larger articles intended for incontinent adult users. The packages can thus be made easier to handle despite the size of the articles they contain.

One embodiment of the invention is characterized in that every second article in the packaging unit is oriented with its fold area in direct contact with the side of the packaging unit, and every other article is oriented with its fold area at a distance from the side of the packaging unit.

According to one embodiment, the articles in the packaging unit can be arranged in pairs in subunits, the articles in every second subunit being arranged with their fold areas in direct contact with the side of the packaging unit, and the articles in every other subunit being arranged with their fold areas at a distance from the side of the packaging unit.

The articles arranged with their fold areas at a distance from the side of the packaging unit are preferably offset by a distance T of 5-50 mm in relation to the articles arranged with their fold areas in direct contact with the side of the packaging unit.

According to yet another preferred embodiment, the articles are offset by a distance T of 5-30 mm, and in a still more preferred embodiment the articles are offset by a distance of 5-15 mm.

A packaging unit according to the invention can be packed in a bag or can be enclosed in a wrapper.

According to one embodiment, the packaging unit can be vacuum-packed.

Packaging units according to the invention can contain babies' diapers, incontinence diapers for incontinent adult users, or catamenial products.

DESCRIPTION OF THE FIGURES

The embodiments of the invention will be described in greater detail below with reference to the figures shown in the attached drawings.

DETAILED DESCRIPTION OF THE PREFERRED EMBODIMENTS

An embodiment of the invention is a packaging unit 17, as is shown in FIGS. 3-6, comprising a number of folded absorbent articles 1.

Absorbent articles 1, included in packaging units 17 according to an embodiment of the present invention, can be so-called all-in-one diapers, pant diapers, belt diapers, or sanitary napkins.

So-called pant diapers are primarily distinguished by the fact that they have already been folded, at the time of production, about a substantially transverse fold line 41 in the crotch portion 23 of the diaper, and have then been joined together at the waist. The area near the fold line 41 constitutes the fold area 11 of the pant diaper. This type of diaper is intended to be applied on a user exactly like a pair of briefs, that is to say pulled up over the legs.

Belt diapers are characterized in that they comprise, in relation to the absorbent part of the diaper, a transverse belt connected either to a front or a rear transverse edge of the diaper. When applying such a belt diaper, the belt is fixed, in a first step, around the user's waist. The absorbent part of the diaper is at this stage hanging loosely from the belt. The absorbent part of the diaper is thereafter guided between the user's legs and secured to the belt, said belt comprising fixing surfaces intended to adhere firmly to the fixing devices arranged on the absorbent part of the diaper near its free transverse edge.

The invention is of course applicable both to babies' diapers and to adults' diapers of the various types described above.

The invention can also be applied to absorbent articles intended for menstruation, designed to be packaged and sold in the folded state.

Figure 1:
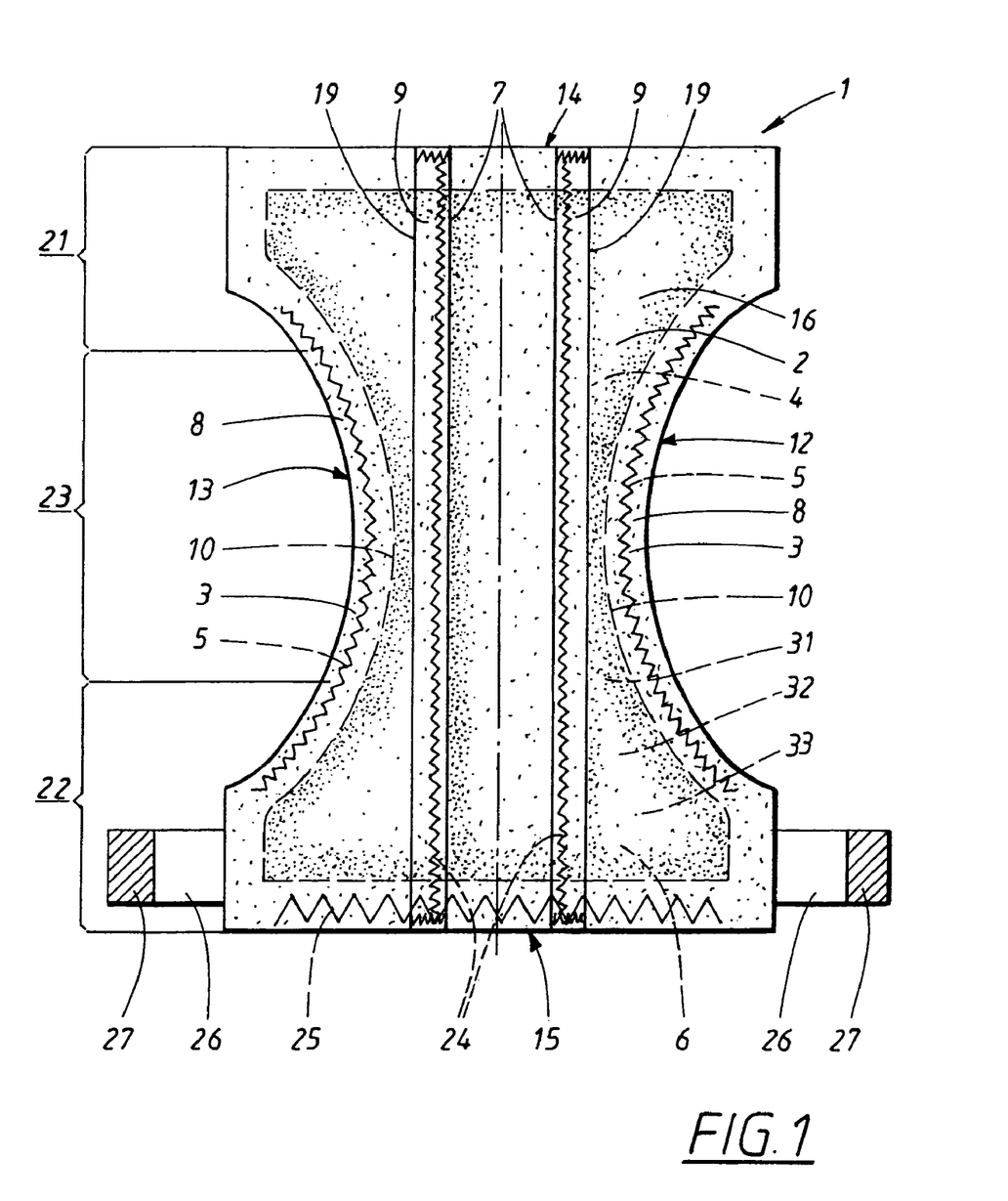
FIG. 1 shows an example of a diaper which can be included in a packaging unit according to an embodiment of the invention.

FIG. 1 shows the main components of a diaper 1 suitable for inclusion in a packaging unit according to an embodiment of the invention.

The diaper 1 is an open diaper for babies and of the so-called all-in-one type. The diaper 1 is in this case not joined together at the waist portion when sold, and instead is designed to be applied round a baby's trunk and thereafter joined together around the waist.

The diaper 1 is substantially hourglass-shaped and has longitudinal edges 12, 13, a front transverse edge 14, and a rear transverse edge 15, and front and rear end portions 21, 22, and a narrower crotch portion 23 located between the end portions 21, 22. During use, the crotch portion 23 is intended to be located at the narrowest area between the baby's thighs.

When the diaper 1 is in use, the front part of the crotch portion 23 and the front end portion 21 function principally as a receiving area for urine, while the rear part of the crotch portion 23 and the rear end portion 22 principally function as a receiving area for faeces.

The diaper 1 comprises a covering sheet 16 having a liquid-permeable covering sheet 2 arranged over that surface of the diaper 1 which during use is intended to face towards the baby, and a liquid-impermeable backing sheet 4 arranged over that surface of the article which during use is intended to face away from the baby, an absorption body 6 enclosed between the liquid-permeable covering sheet 2 and the backing sheet 4, and side flaps 3 arranged outside the absorption body 6.

The liquid-permeable covering sheet 2 extends outside the absorption body 6 along the whole periphery of the absorption body 6. The liquid-permeable covering sheet 2 can consist of any material suitable for the purpose. Examples of commonly used liquid-permeable covering materials are nonwoven textile materials, perforated plastic films, meshes of plastic or textile, and liquid-permeable foam sheets. Liquid-permeable covering sheet materials also occur which consist of continuous thin fibres extending substantially in the longitudinal or transverse direction of the article. Laminates consisting of two or more of the abovementioned possible covering materials are also commonly used, and also covers consisting of different materials within different parts of the surface.

Diapers 1 comprising absorption bodies 6 which have particularly high strength and resistance to wear can even function without any extra liquid-permeable covering sheet being required on that side of the diaper which faces towards the baby during use.

The backing sheet 4 consists of a laminate 31 comprising a liquid-impermeable plastic film 32 arranged towards the absorption body 6 and a nonwoven sheet 33, said nonwoven sheet 33 being arranged away from the absorption body 6 so that the outside of the diaper 1 is more like clothing during use of the diaper 1. The backing sheet 4 extends outside the absorption body 6 along the entire periphery of the absorption body 6.

The backing sheet 4 of babies' diapers 1 usually consists of liquid-impermeable plastic films or of laminates in which liquid-impermeable plastic films are included, but other types of liquid-impermeable backing sheets are also possible. Examples of alternative types of liquid-impermeable materials are nonwoven materials which have been made liquid-impermeable, liquid-impermeable foam sheets, liquid-impermeable adhesive, or similar. Nowadays it is also common for the backing sheet 4 to consist of a vapour-permeable plastic film, or of a laminate in which a vapour-permebale plastic film is included as liquid barrier. The vapour-permeable plastic film must of course be liquid-impermeable in order to prevent passage of liquid from the absorption body. The nonwoven sheet 33 is designed so that it functions as a receiving sheet for the male component of a hook-and-loop system. The nonwoven sheet 33 in this case comprises closed loops or the like.

The liquid-permeable covering sheet 2 and the backing sheet 4 are connected to one another outside the absorption body 6, along the entire periphery of the absorption body 6. The connection between the sheets 2, 4 can be effected in a number of different ways. Examples of connection methods are gluing, meltbonding, ultrasound welding, or similar.

Elastic members 3 of the disposable diaper 1 substantially extend in the longitudinal direction of the diaper 1. The elastic members 5 function as leg elastic and have the role of preventing liquid and excrement from leaking out through the longitudinally extending side edges 12, 13 and in this way they form outer liquid barriers 8 in conjunction with the surrounding layers. The elastic members 5 consist of one or more elastic threads which, in the stretched state, have been applied between the liquid-permeable covering sheet 2 and the backing sheet 4, at least in the crotch portion 23 of the diaper 1. The elastic members 5 are connected to the backing sheet 4 and the covering sheet 2 by gluing, ultrasonic welding or similar.

In alternative embodiments, the elastic devices can be arranged on that side of the side flaps 3 which is intended to face towards the user during use, or on the opposite side of the side flaps, and are of course then only connected to the liquid-permeable covering sheet 2 or the backing sheet 4.

In alternative embodiments, the elastic devices can comprise elastic band material, for example made of foam material.

The hourglass-shaped absorption body 6 can be made up of one or more layers of cellulose fluff pulp. The cellulose fluff pulp can be mixed with fibres or particles of a superabsorbent polymer material of the type which chemically binds large amounts of liquid upon absorption, thus forming a liquid-containing gel. The absorption body 6 can also comprise superabsorbent polymer material arranged in a layer inside the absorption body or near the surface or surfaces of the absorption body. The absorption body 6 can also include further components for improving the properties of the absorption body 6. Examples of such components are binder fibres, various types of liquid-spreading layers or fibres, shape-stabilizing components, reinforcement fibres, or similar. The absorption body 6 can of course also consist of other types of absorption material, such as absorbent nonwoven material, absorbent foam, textile material, peat, or mixtures of various types of absorption material.

Diapers of the type in question can also include special layers for rapidly taking up a large amount of liquid and temporarily storing it before passing the temporarily stored liquid to other parts of the absorption body 6. Such layers are normally arranged between the liquid-permeable covering sheet 2 of the diaper 1 and the absorption body 6. No receiving layer is shown in any of the figures.

To further prevent liquid or faeces from leaking out via the side edges 12, 13 of the diaper 1, said diaper 1 is provided with inner side leakage barriers 9 on the side intended to face towards the baby during use. The inner side leakage barriers 9 are arranged lying near the longitudinal edges 10 of the absorption body 6 and extend substantially in the longitudinal direction of the diaper 1. The side leakage barriers 9 are made of double-folded separate material strips, the fold edges 7 constituting the ridges of the side leakage barriers 9. The branches of the double-folded material strips are fixed to the covering sheet 2 and constitute fixed edges 19 of the side leakage barriers. In the front end portion 21 and rear end portion 22 of the diaper 1, the side leakage barriers 9 are turned down and connected to the covering sheet 2 across their entire widths.

The inner side leakage barriers 9 comprise elastic elements 24 connected to the inner side leakage barriers 9 in the tensioned state. The elastic elements 24 are preferably arranged near the free edges of the side leakage barriers 9. When the tensioned elastic elements 24 are released, they contract together with the free edges of the side leakage barriers 9, and the inner side leakage barriers 9 are thus brought into a raised configuration directed away from the liquid-permeable covering sheet 2 in the crotch portion 23 of the diaper 1, where the side leakage barriers 9 are only connected to the covering sheet 2 at their respective fixed edges 19.

The rear and/or front portions 22, 21 of the diaper 1 can also be provided with so-called waist elastic 25 which consists of elastic devices arranged along the front transverse edge 14 and/or rear transverse edge 15 of the diaper 1 in order to allow the diaper to close gently and flexibly about the user's waist. In the present illustrative embodiment, only the rear end portion 22 of the diaper 1 is provided with waist elastic 25 in the form of a thin strip of an elastic foam material which is fixed with glue between the backing sheet 4 and the liquid-permeable covering sheet 2. The waist elastic 25 is applied in the stretched state between the layers in order to generate a holding force stretching the diaper 1 about the user's waist.

The rear end portion 22 is provided with two soft and non-elastic fastening tabs 26 for fixing the diaper 1 about the baby's waist, with one fastening tab 26 arranged on each side portion of the rear end portion 22. The fastening tabs 26 are expediently made of a very soft and non-elastic material, for example a single nonwoven layer or a laminate. During use, the fastening tabs 26 connect the rear end portion 22 to the front end portion 21.

The fastening tabs 26 comprise fixing devices 27, said fixing devices 27 preferably consisting of a male part of a hook-and-loop system and being secured to the fastening tabs 26 with glue or the like. The fixing devices 27 are arranged on that side of the respective securing tab 26 which, during use, faces towards that surface on the front end portion 21 which faces away from the baby during use.

In alternative embodiments, the securing tabs 26 can be elastic. The fixing devices 27 of the securing tabs 26 can, in some embodiments, consist of female parts of a hook-and-loop system, pressure-sensitive adhesive or the like.

When applying the diaper 1 about a baby's waist, the rear end portion 22 is coupled to the front end portion 21 by connecting the fixing devices 27 of the securing tabs 26 to the front end portion 21. Since the diaper 1 has a backing sheet 4 comprising a nonwoven layer 33 functioning as receiving layer for a hook-and-loop material of the male type, the fixing device 27 can be secured anywhere on the backing sheet 4 of the diaper 1.

For alternative embodiments in which the backing sheet 4 of the diaper 1 is not adapted to cooperate with the fixing devices 27 of the securing tabs 26, special fixing sites are expediently arranged on the backing sheet 4 of the diaper 1 in the front end portion 21. The special fixing sites in this case consist of separate material sections of suitable shape and size, said material sections comprising material that can be connected to the fixing devices 27 of the securing tabs 26. The separate material sections are applied on the backing sheet 4 by gluing, thermal welding, ultrasonic welding or similar. The fixing sites are arranged parallel to and close to the front transverse edge 14 of the diaper 1.

Diapers 1 which comprise fixing devices 27 of the adhesive type, and whose backing sheet 4 comprises a nonwoven layer 33, normally have special fixing sites in the front end portion 21 which are designed for receiving adhesive fixing devices 27. Special fixing sites in such cases comprise a plastic surface or the like and usually consist of one or more separate material sections of suitable shape and size which have been applied at suitable sites on the backing sheet 4 by gluing, thermal welding, ultrasonic welding or the like. It is also common for diapers 1, equipped with adhesive fixing devices 27, to have a backing sheet 4 consisting only of plastic film or the like, in which case the adhesive fixing device 27 can be secured directly to the backing sheet 4 of the diaper 1 anywhere on the backing sheet 4.

Figure 2:
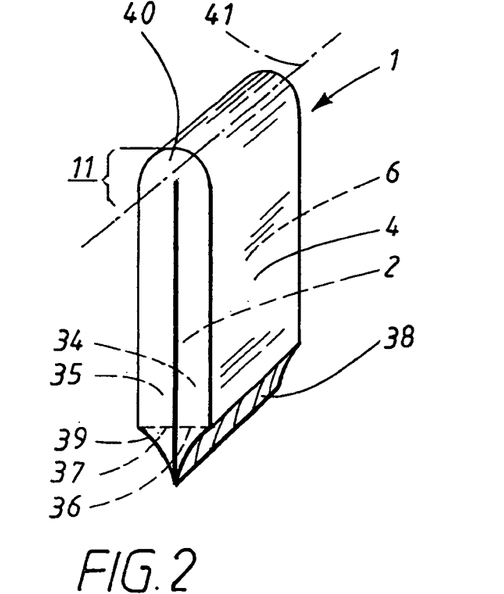
FIG. 2 shows a diaper configured for inclusion in a packaging unit according to an embodiment of the invention.

FIG. 2 shows a diagrammatic illustration of a diaper 1 folded in the same way as diapers 1 included in a packaging unit 17 according to an embodiment of the invention. The diaper 1 is folded once, along a substantially transverse fold line 41, said fold line 41 being arranged substantially at the center of the diaper 1 as viewed in the longitudinal direction of the diaper 1. The diaper 1 comprises a fold area 11 near the fold line 41. The diaper 1 is shown diagrammatically, and some of the components of the diaper 1 have been omitted. Examples of components not included in FIG. 2 are securing tabs 26 and waist elastic 25.

The absorption body 6 has a fold area 40 which coincides with the fold area 11 of the diaper. The absorption body 6 has a front transverse edge 36 and a rear transverse edge 37. The front end seal 38 of the diaper 1 is arranged outside the front transverse edge 36 of the absorption body 6, and the rear end seal 39 of the diaper 1 is arranged outside the rear transverse edge 37. The end seals 38, 39 comprise the liquid-permeable covering sheet 2 and the backing sheet 4, said two sheets 2, 4 being connected to one another by gluing. In alternative embodiments, the end seals 38, 39 can be arranged in an alternative way, for example a separate covering sheet arranged outside the backing sheet can be included in the end seals 38, 39.

The absorption body 6, which represents the greatest part of the thickness of the diaper 1, comprises principally what is called airlaid fluff pulp, which is especially sensitive to damage in the form of permanent fold notches if it is pressed together hard where the fluff pulp is folded.

The most common situation, especially for smaller diapers 1 intended for babies, is that they are folded along a transverse fold line 41, substantially at the center of the diaper 1 in its longitudinal direction, when they are being packaged. The fold area 11 around the fold line 41 is thus sensitive to formation of permanent fold notches when the diaper 1 is exposed to strong compression at right angles to its material during packaging of the diaper 1.

An especially disadvantageous combination as regards formation of permanent fold notches is strong compression of the diaper 1 in combination with a high moisture content, that is to say a moisture content in excess of 10%. When a diaper 1 which has been compressed strongly during packaging is later removed from its package at the time of use, it is not uncommon for the diaper 1 to have a permanent and hard fold notch located in that part of the diaper 1 normally placed in the user's crotch area during use of the diaper 1.

Figure 2A:
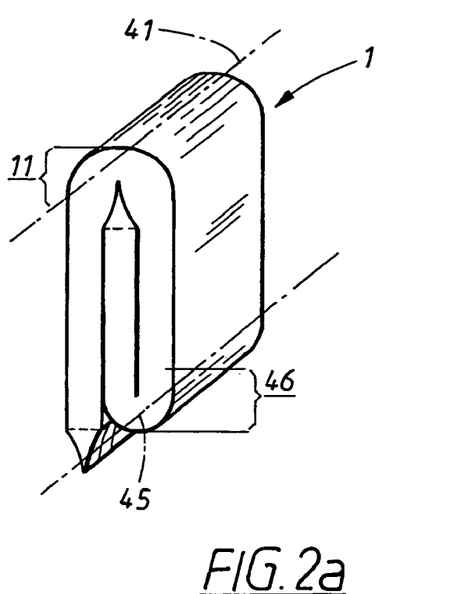
FIG. 2a shows a diaper differently configured for inclusion in a packaging unit according to an embodiment of the invention.

FIG. 2a shows a diagrammatic illustration of a diaper 1 configured in an alternative manner and intended to be included in an alternative packaging unit 17 according to an embodiment of the invention. This way of folding diapers 1 in three parts is especially common for larger diapers 1 intended for incontinent adult users, although it is also used for smaller diapers 1 intended for toddlers. The diaper 1 is folded along a first substantially transverse fold line 41 and along a second substantially transverse fold line 45. The fold lines 41, 45 are in this case arranged at a distance from the center of the diaper 1, viewed in the longitudinal direction of the diaper 1. This folding method involves the diaper 1 being folded twice, so that the folded diaper 1 has a first fold area 11 near the first transverse fold line 41, and a second fold area 46 near the second transverse fold line 45.

Alternatively, a diaper 1 can of course be folded around one or more further fold lines.

Figure 3:
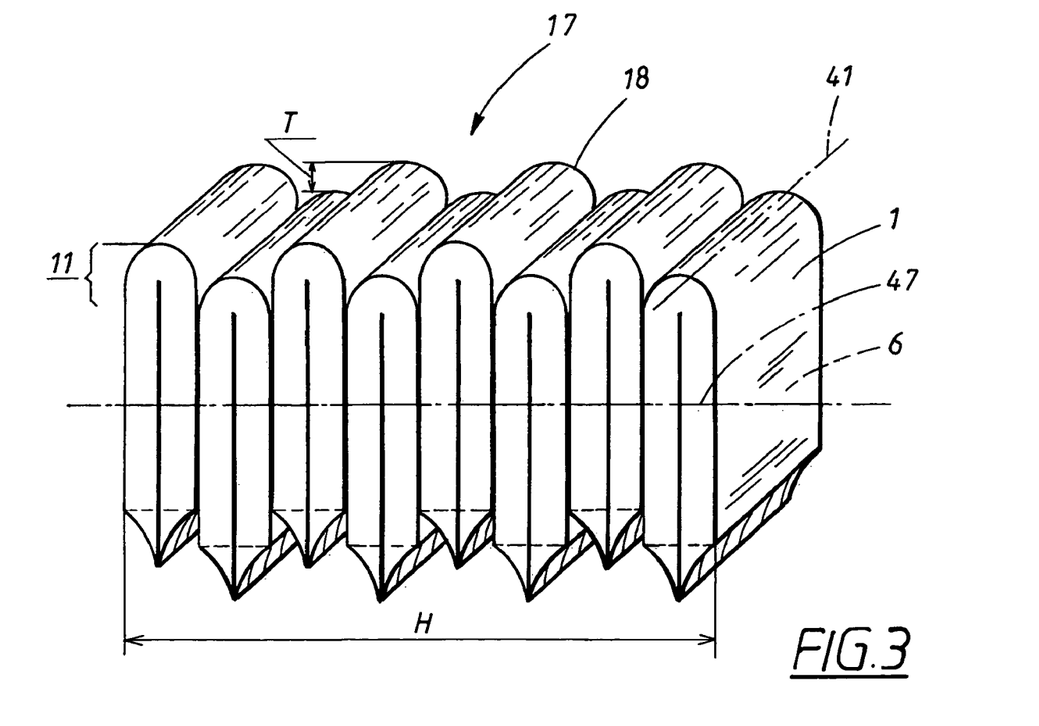
FIG. 3 shows a first embodiment of a packaging unit according to an embodiment of the invention.
Figure 4:
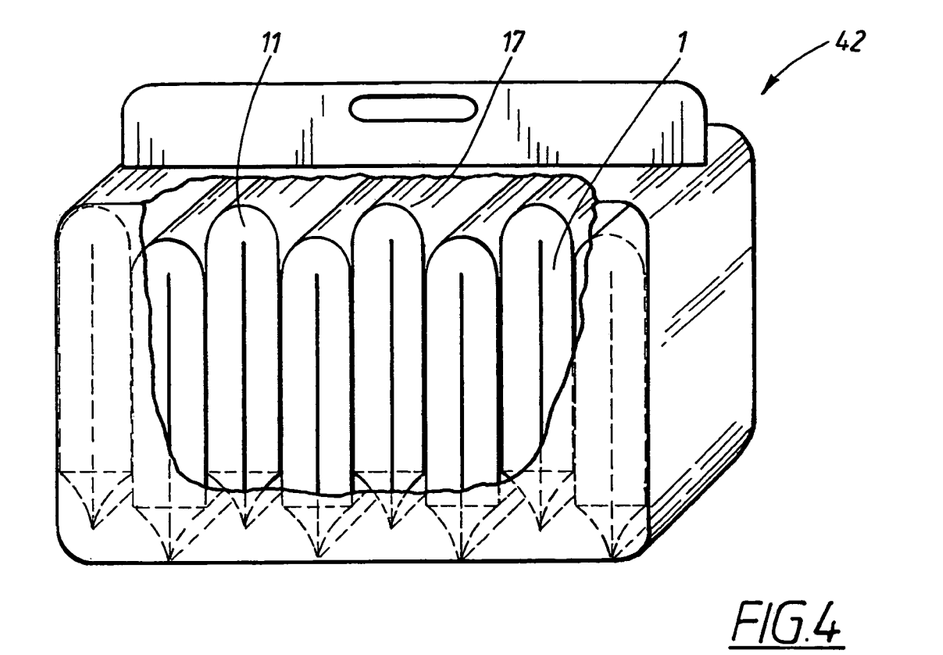
FIG. 4 shows a packaging comprising a packaging unit according to an embodiment of the invention.

FIG. 3 shows how the diapers 1, folded according to FIG. 2, are configured in a packaging unit 17 according to a first embodiment of the invention, and FIG. 4 shows the packaging unit 17 introduced into a package 42. The packaging unit 17 comprises eight diapers 1, but packaging units containing a greater or smaller number of diapers 1 are of course conceivable within the scope of the invention.

The package 42 in FIG. 4 comprises a plastic or paper bag and contains one packaging unit 17. In alternative embodiments, the package 42 can contain several packaging units 17 arranged side by side or on top of one another. It is also possible to have large packages 42 containing packaging units 17 arranged both side by side and in several layers on top of one another.

The diapers 1 can of course be arranged in an alternative way in the package 42, for example the fold areas 11 of the diapers 1 can be oriented towards the bottom of the bag or towards either the front or back of the bag.

A packaging unit 42 can alternatively be enclosed in a wrapper, as indicated in patent specification WO 93/16925. The packaging unit provided with the wrapper can then be enclosed in a bag of suitable material or can be supplied without any extra covering material. It is also conceivable to vacuum-pack one or more packaging units 17 according to an embodiment of the invention in a substantially air-tight plastic package.

The packaging unit 17 comprises a side 18, and the diapers 1 included in the packaging unit 17 are oriented with their fold lines 41 parallel to the side 18 of the packaging unit 17, and with their fold areas 11 oriented towards the side 18 of the packaging unit 17. The side 18 of the packaging unit 17 is defined as the plane at a tangent to the fold lines 41 of those diapers 1 in the packaging unit 17 which are arranged with their fold areas 11 farthest away from the longitudinal center line 47 of the packaging unit 17.

The packaging unit 17 is primarily distinguished by the fact that every second diaper 1 in the packaging unit 17 is arranged with its fold area 11 at the side 18 of the packaging unit 17 and every other diaper 1 is arranged with its fold area 11 at a distance T from the side 18 of the packaging unit 17. Every other diaper 1 has thus been offset by a distance T in the plane of the folded diapers 1 at right angles to the fold line 41 of the respective diaper 1.

The fold areas 11 of those diapers 1 whose fold areas 11 are arranged farthest away from the center line 47 of the packaging unit 17 are located outside the fold areas 11 of adjoining diapers 1 whose fold areas 11 are located nearer to the center line 47 of the packaging unit 17. The fold areas 11 of every second diaper 1 project by a distance T of 5 to 50 mm, preferably 5 to 30 mm, and most preferably 5 to 15 mm, outside of adjoining diapers 1.

When the packaging unit 17 is to be introduced into a package 42, the diapers 1 of the packaging unit 17 will be pressed together as much as possible in order to minimize the height H of the packaging unit and thus obtain a package which is as small as possible. At the same time, one will want to avoid permanent fold notches in the fold areas of the diapers 1, that is to say in the crotch portion of the diaper, upon compression. The compression is effected at right angles to the material layers of the folded diapers 1, thus reducing the thickness of the diapers 1. The reduction in the thickness of the diapers largely comes from a reduction in the thickness of the absorption bodies 6.

When a packaging unit 17 comprising offset diapers 1 according to an embodiment of the invention is compressed, it is thus possible to avoid pressing the fold areas 11 of all the diapers 1 together, and this means that one also avoids creating permanent fold notches in the fold areas 11 of the diapers.

During compression, the fold areas 11 of the diapers 1 situated farthest away from the longitudinal center line 47 of the packaging unit 17 are allowed to take up the free space which has been created by the fact that the diapers 1 on both sides of and near the fold lines 11 are offset towards the longitudinal center line 47 of the packaging unit 17. This can be put another way by saying that the fold areas of the diapers 1 have been given space to expand laterally during compression of the packaging unit 17.

It has also been found that the diapers 1 with fold areas 11 nearer the center line 47 of the packaging unit 17, that is to say the diapers 1 whose fold areas 11 are surrounded by diapers 1 on both sides, are better protected from formation of permanent fold notches, during compression of the packaging unit 17, compared with compression of traditional packaging units in which all the fold areas lie next to one another at the same distance from the center line 47. This is because the surrounding diapers 1 lie against the fold areas 11 with surfaces which are partially resilient at right angles to their material layers. These fold areas 11, located between diapers 1, are therefore also allowed to expand slightly in the lateral direction during compression of the packaging unit 17. The expansion is sufficient to avoid permanent fold notches in the fold areas 11 of the diapers 1, even in the case of strong compression.

Consequently, diapers 1 configured in packaging units 17 according to an embodiment of the invention can be compressed substantially more strongly when they are being packed, without permanent fold notches occurring at the fold areas 11 of the diapers 1.

Increased compression means that the height H of the packaging unit 17 is reduced, while its width is slightly increased. However, the reduction in height H markedly exceeds the increase in width of the packaging unit 17, for which reason the total volume of the packaging unit 17 is decreased.

Figure 5:
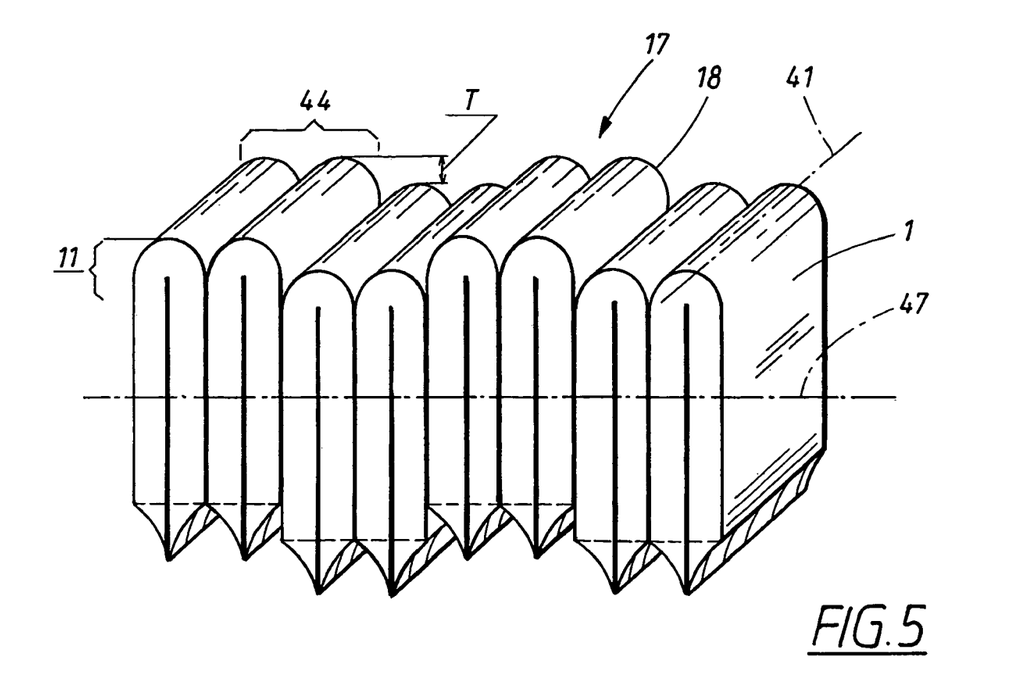
FIG. 5 shows a second embodiment of a packaging unit according to an embodiment of the invention.

FIG. 5 shows how the diapers are configured in a packaging unit 17 according to an alternative second embodiment of the invention. The packaging unit 17 contains eight diapers 1, but it can of course alternatively contain a greater or smaller number of diapers 1. The packaging unit 17 has a side 18. The diapers 1 are oriented with their fold lines 41 parallel to the side 18 of the packaging unit 17, and with their fold areas 11 oriented towards the side 18 of the packaging unit 17. The side 18 of the packaging unit 17 is defined as the plane at a tangent to the fold lies 41 of those diapers 1 in the packaging unit 17 which are arranged with their fold areas 11 farthest away from the center line 47.

The diapers 1 in the packaging unit 17 are arranged two by two in subunits 44. Every second subunit 44 is arranged with its fold areas 11 near the side 18 of the packaging unit 17, and every other subunit 44 is arranged with its fold areas 11 at a distance T from the side 18 of the packaging unit 17. Every second subunit 44 has been offset a distance T in the plane of the folded diapers 1, at right angles to the fold lines 41 of the diapers 1. Those subunits 44 which comprise diapers 1 whose fold areas 11 are arranged farthest away from the center line 47 of the packaging unit 17 thus have fold areas 11 situated outside the fold areas 11 of diapers 1 of adjoining subunits 44. The fold areas 11 of the diapers 1 in every second subunit 44 project by a distance T of 5 to 50 mm, preferably 5 to 30 mm, and most preferably 5 to 15 mm, outside the diapers 1 of adjacent subunits 44.

When the packaging unit 17 according to this embodiment is to be compressed, for example for introduction into a package 42, the fold areas of those diapers 1 which are arranged with their fold areas 11 farthest away from the center line 47 of the packaging unit 17 are able to expand laterally. One of the two diapers 1 included in such a subunit 44 is allowed to expand in one direction, while the other diaper 1 in the same subunit 44 is allowed to expand in the opposite direction. Every other subunit 44 comprises diapers 1 whose fold areas 11 are arranged nearer the center line 47 of the packaging unit 17. The fold areas 11 of these diapers 1 touch the diapers 1 in adjoining subunits 44. This means that these diapers 1 cannot expand completely freely, but, because the contact surfaces of the adjoining diapers 1 against the fold areas 11 consist of areas which are relatively resilient upon compression of the packaging unit 17, permanent fold notches are avoided in the fold areas 11 of these diapers 1 too. One diaper 1 is allowed to expand towards the partially resilient material sheet of the diaper 1 lying next to it in the next subunit 44, and the second diaper 1 is allowed to expand in the same way towards the partially resilient material sheet of the diaper 1 lying next to it.

Consequently, diapers 1 configured in packaging units 17 according to this embodiment of the invention can also be strongly compressed, without permanent fold notches arising in the fold areas 11 of the diapers 1.

When a packaging unit 17 according to this embodiment is to be introduced into a bag, or when a wrapper is to be applied around the packaging unit 17, this is done in the same way as for a packaging unit according to the first embodiment above.

Figure 6:
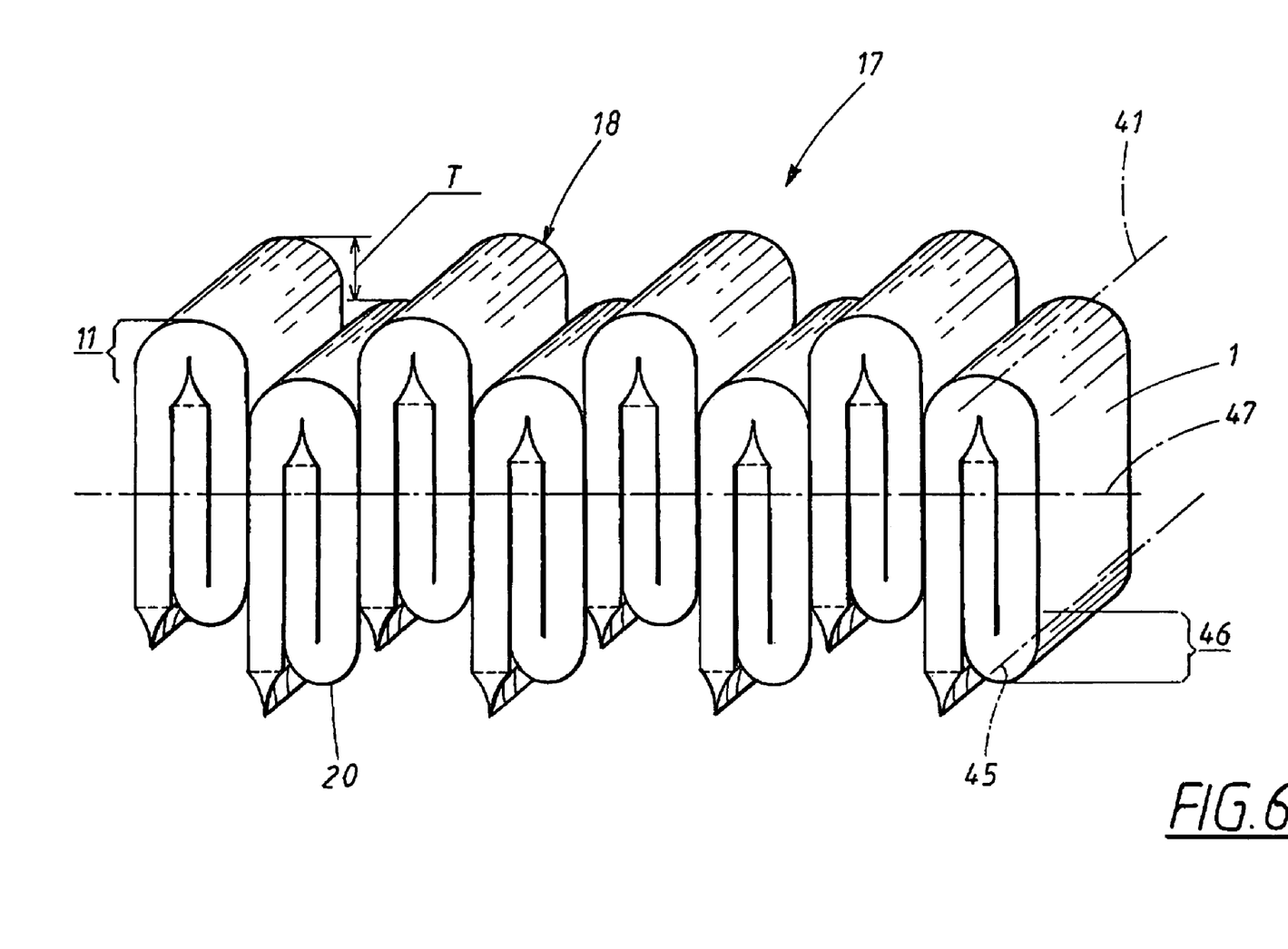
FIG. 6 shows a third embodiment of a packaging unit according to an embodiment of the invention.

FIG. 6 shows how diapers 1, folded according to FIG. 2a, are configured in a packaging unit 17 according to a third alternative embodiment of the invention. The packaging unit 17 contains eight diapers 1, but it can alternatively contain a greater or smaller number of diapers 1. The packaging unit 17 has a first side 18, and the diapers 1 included in the packaging unit 17 are oriented with their first substantially transverse fold lines 41 parallel to the first side 18 of the packaging unit, and with their first fold areas 11 oriented towards the first side 18 of the packaging unit 17. The packaging unit 17 further comprises a second side 20, and the diapers 1 included in the packaging unit 17 are oriented with their second substantially transverse fold lines 45 parallel to the second side 20 of the packaging unit, and with their second fold areas 46 oriented towards the second side 20 of the packaging unit 17. The first side 18 of the packaging unit 17 is defined as the plane at a tangent to the fold lines 41 of those diapers 1 in the packaging unit 17 which are arranged with their first fold areas 11 farthest away from the center line 47. The second side 20 of the packaging unit 17 is defined as the plane at a tangent to the fold lines 45 of those diapers 1 in the packaging unit 17 which are arranged with their second fold areas 46 farthest away from the center line 47.

The packaging unit 17 is distinguished by the fact that every second diaper 1 is arranged with its first fold area 11 at the first side 18 of the packaging unit 17, and every other diaper 1 is arranged with its first fold area 11 at a distance T from the first side 18 of the packaging unit 17. Every other diaper 1 has thus been offset by a distance T in the plane of the folded diapers 1, at right angles to the fold lines 41, 45 of the respective diaper 1. The first fold areas 11 of those diapers 1 whose first fold areas 11 are arranged farthest away from the center line 47 of the packaging unit 17 are located outside the first fold areas 11 of adjoining diapers 1 whose first fold areas 11 are located nearer to the center line 47 of the packaging unit 17. The first fold areas 11 of every second diaper 1 project by a distance T of 5 to 50 mm, preferably 5 to 30 mm, and most preferably 5 to 15 mm, outside of adjoining diapers 1.

Consequently, the second fold areas 46 of those diapers 1 arranged at the second side 20 of the packaging unit 17 are also offset in relation to one another. Those diapers 1 in the packaging unit 17 which are arranged with their first fold area 11 at a distance T from the first side 18 of the packaging unit 17 are thus arranged with their second fold area 46 at the second side 20 of the packaging unit 17, and those diapers 1 which are arranged with their first fold area 11 at the first side 18 of the packaging unit 17 are thus arranged with their second fold areas 46 at a distance from the second side 20 of the packaging unit.

The fact that the diapers 1 are offset in the packaging unit 17 means that during compression of the packaging unit 17, for example when packing the latter in a bag, no fold areas 11, 46 are pressed directly against any adjoining fold area 11, 46. The fold areas 11, 46 of the diapers 1 are thus exposed to compression in the same way as has been described above for the first embodiment, which means that every second fold area 11, 46 is allowed to freely expand to the sides and every other fold area 11, 46 is allowed to expand towards more resilient parts of the diapers 1 lying next to it. Expansion towards more resilient parts of adjoining diapers 2 permits sufficient expansion to avoid formation of permanent fold notches in the fold areas 11, 46 of the diapers 1, even upon strong compression of the packaging unit 17.

The invention also includes all conceivable combinations of the illustrative embodiments described.

Moreover, the invention is not limited to the abovementioned illustrative embodiments, and instead it can of course be applied to other embodiments within the scope of the attached patent claims and equivalents thereof.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A packaging unit comprising at least one side, which packaging unit comprises a number of absorbent articles in a single row, each absorbent article being folded at least once along a fold line, each article having at least one fold area, the fold lines of the articles being arranged parallel to the side of the packaging unit, and the fold areas of the articles being oriented towards the side of the packaging unit, the fold areas of a first group of the absorbent articles are arranged at a distance from the side of the packaging unit, and the fold areas of a second group of the absorbent articles are arranged in direct contact with the side of the packaging unit.

2. The packaging unit according to claim 1, wherein the fold lines of the absorbent articles are arranged substantially at a center of the articles in the longitudinal direction of the articles.

3. The packaging unit according to claim 1, wherein the fold lines of the absorbent articles are arranged at a distance from a center of the articles in the longitudinal direction of the articles.

4. The packaging unit according to claim 3, wherein the absorbent articles are folded about a second fold line, and the absorbent articles further comprise a second fold area.

5. The packaging unit according to claim 1, wherein every second folded article is oriented with its fold area in direct contact with the side of the packaging unit, and every other folded article is oriented with its fold area at a distance from the side of the packaging unit.

6. The packaging unit according to claim 1, wherein the articles are arranged in subunits of two articles, the articles in every second subunit being arranged with their fold areas in direct contact with the side of the packaging unit, and the articles in every other subunit being arranged with their fold areas at a distance from the side of the packaging unit.

7. The packaging unit according to claim 1, wherein the articles arranged with their fold areas at a distance from the side of the packaging unit are offset by a distance of 5-50 mm in relation to articles arranged with their fold areas in direct contact with the side of the packaging unit.

8. The packaging unit according to claim 1, wherein the articles arranged with their fold areas at a distance from the side of the packaging unit are offset by a distance of 5-30 mm in relation to articles arranged with their fold areas in direct contact with the side of the packaging unit.

9. The packaging unit according to claim 1, wherein the articles arranged with their fold areas at a distance from the side of the packaging unit are offset by a distance of 5-15 mm in relation to articles arranged with their fold areas in direct contact with the side of the packaging unit.

10. The packaging unit according to claim 1, wherein the packaging unit is packed in a bag.

11. The packaging unit according to claim 1, wherein the packaging unit is surrounded by a wrapper.

12. The packaging unit according to claim 1, wherein the packaging unit is vacuum-packed.

13. The packaging unit according to claim 1, wherein the absorbent articles are babies' diapers.

14. The packaging unit according to claim 1, wherein the absorbent articles are incontinence diapers.

15. The packaging unit according to claim 1, wherein the absorbent articles are catamenial products.

16. The packaging unit according to claim 1, wherein the fold lines are substantially transverse fold lines.

17. A packaging unit comprising a plurality of absorbent articles in a single row, each absorbent article being folded at least once along a fold line in a fold area, the fold lines of the articles being arranged parallel to each other, and the fold areas of the articles being oriented towards a same side of the packaging unit, the fold areas of a first group of the absorbent articles are offset with respect to the fold areas of a second group of the absorbent articles of the packaging unit.

18. The packaging unit according to claim 17, wherein the fold lines of the absorbent articles are arranged substantially at a center of the articles in the longitudinal direction of the articles.

19. The packaging unit according to claim 17, wherein the fold lines of the absorbent articles are arranged at a distance from a center of the articles in the longitudinal direction of the articles.

20. The packaging unit according to claim 19, wherein the absorbent articles are folded about a second substantially transverse fold line, the absorbent articles comprising a second fold area.

21. The packaging unit according to claim 17, wherein every second folded article is oriented with its fold area in direct contact with a side of the packaging unit, and every other folded article is oriented with its fold area at a distance from the side of the packaging unit.

22. The packaging unit according to claim 17, wherein the articles are arranged in subunits of two articles, the articles in every second subunit being arranged with their fold areas in direct contact with a side of the packaging unit, and the articles in every other subunit being arranged with their fold areas at a distance from the side of the packaging unit.

23. The packaging unit according to claim 21, wherein the articles arranged with their fold areas at a distance from the side of the packaging unit are offset by a distance of 5-50 mm in relation to articles arranged with their fold areas in direct contact with the side of the packaging unit.

24. The packaging unit according to claim 21, wherein the articles arranged with their fold areas at a distance from the side of the packaging unit are offset by a distance of 5-30 mm in relation to articles arranged with their fold areas in direct contact with the side of the packaging unit.

25. The packaging unit according to claim 21, wherein the articles arranged with their fold areas at a distance from the side of the packaging unit are offset by a distance of 5-15 mm in relation to articles arranged with their fold areas in direct contact with the side of the packaging unit.

26. The packaging unit according to claim 22, wherein the articles arranged with their fold areas at a distance from the side of the packaging unit are offset by a distance of 5-50 mm in relation to articles arranged with their fold areas in direct contact with the side of the packaging unit.

27. The packaging unit according to claim 22, wherein the articles arranged with their fold areas at a distance from the side of the packaging unit are offset by a distance of 5-30 mm in relation to articles arranged with their fold areas in direct contact with the side of the packaging unit.

28. The packaging unit according to claim 22, wherein the articles arranged with their fold areas at a distance from the side of the packaging unit are offset by a distance of 5-15 mm in relation to articles arranged with their fold areas in direct contact with the side of the packaging unit.

29. The packaging unit according to claim 17, wherein the packaging unit is packed in a bag.

30. The packaging unit according to claim 17, wherein the packaging unit is surrounded by a wrapper.

31. The packaging unit according to claim 17, wherein the packaging unit is vacuum-packed.

32. The packaging unit according to claim 17, wherein the absorbent articles are babies' diapers.

33. The packaging unit according to claim 17, wherein the absorbent articles are incontinence diapers.

34. The packaging unit according to claim 17, wherein the absorbent articles are catamenial products.

35. A method of packaging a unit of a plurality of absorbent articles, each absorbent article being folded at least once along a fold line in a fold area, the method comprising arranging the plurality of articles in a single row such that the fold lines of the articles are parallel to each other, and the fold areas of the articles are oriented towards a same direction, and further arranging the plurality of articles such that the fold areas of a first group of the absorbent articles are offset with respect to the fold areas of a second group of the absorbent articles of the packaging unit.

36. The method according to claim 35, wherein the fold lines of the absorbent articles are arranged substantially at a center of the articles in the longitudinal direction of the articles.

37. The method according to claim 35, wherein the fold lines of the absorbent articles are arranged at a distance from a center of the articles in the longitudinal direction of the articles.

38. The method according to claim 37, wherein the absorbent articles are folded about a second substantially transverse fold line, the absorbent articles comprising a second fold area.

39. The method according to claim 35, wherein every second folded article is oriented with its fold area in direct contact with a side of a packaging unit, and every other folded article is oriented with its fold area at a distance from the side of the packaging unit.

40. The method according to claim 35, wherein the articles are arranged in subunits of two articles, the articles in every second subunit being arranged with their fold areas in direct contact with a side of a packaging unit, and the articles in every other subunit being arranged with their fold areas at a distance from the side of the packaging unit.

41. The method according to claim 39, wherein the articles arranged with their fold areas at a distance from the side of the packaging unit are offset by a distance of 5-50 mm in relation to articles arranged with their fold areas in direct contact with the side of the packaging unit.

42. The method according to claim 39, wherein the articles arranged with their fold areas at a distance from the side of the packaging unit are offset by a distance of 5-30 mm in relation to articles arranged with their fold areas in direct contact with the side of the packaging unit.

43. The method according to claim 39, wherein the articles arranged with their fold areas at a distance from the side of the packaging unit are offset by a distance of 5-15 mm in relation to articles arranged with their fold areas in direct contact with the side of the packaging unit.

44. The method according to claim 40, wherein the articles arranged with their fold areas at a distance from the side of the packaging unit are offset by a distance of 5-50 mm in relation to articles arranged with their fold areas in direct contact with the side of the packaging unit.

45. The method according to claim 40, wherein the articles arranged with their fold areas at a distance from the side of the packaging unit are offset by a distance of 5-30 mm in relation to articles arranged with their fold areas in direct contact with the side of the packaging unit.

46. The method according to claim 40, wherein the articles arranged with their fold areas at a distance from the side of the packaging unit are offset by a distance of 5-15 mm in relation to articles arranged with their fold areas in direct contact with the side of the packaging unit.

47. The method according to claim 35, further comprising packing the unit in a bag.

48. The method according to claim 35, further comprising surrounding the unit by a wrapper.

49. The method according to claim 35, further comprising vacuum-packing the unit.

50. The method according to claim 35, wherein the absorbent articles are babies' diapers.

51. The method according to claim 35, wherein the absorbent articles are incontinence diapers.

52. The method according to claim 35, wherein the absorbent articles are catamenial products.

* * * * *